US008192475B2

(12) United States Patent
Anderson et al.

(10) Patent No.: US 8,192,475 B2
(45) Date of Patent: Jun. 5, 2012

(54) WARMING DEVICE CONSTRUCTIONS WITH A PONCHO-TYPE PATIENT GOWN (75) Inventors: Thomas P. Anderson, Savage, MN (US); Jared J. Balthazor, St. Francis, MN (US); Paul T. Kennedy, Burnsville, MN (US); Andrew J. McGregor, Minneapolis, MN (US); Christopher A. Miller, Apple Valley, MN (US); Mark A. Poppen, Eden Prairie, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 345 days.

(21) Appl. No.: 12/653,825

(22) Filed: Dec. 21, 2009

(65) Prior Publication Data
US 2010/0179624 A1    Jul. 15, 2010

Related U.S. Application Data (63) Continuation-in-part of application No. 10/508,319, filed as application No. PCT/US03/11128 on Apr. 10, 2003, now Pat. No. 7,837,721.

(60) Provisional application No. 60/371,314, filed on Apr. 10, 2002.

(51) Int. Cl.
*A61F 7/00*    (2006.01)
(52) U.S. Cl. ................ 607/107; 607/104; 607/114
(58) Field of Classification Search .................. 607/104, 607/107, 108, 112, 114
See application file for complete search history.

(56) References Cited

U.S. PATENT DOCUMENTS

| 2,512,559 | A | 6/1950 | Williams | 5/347 |
| 2,573,414 | A | 10/1951 | Dunn | 128/144 |
| 2,826,758 | A | 3/1958 | Kahn | 2/61 |
| 3,468,299 | A | 9/1969 | D'Amato | 126/204 |
| 3,610,323 | A | 10/1971 | Troyer | 165/46 |
| 3,757,366 | A | 9/1973 | Sacher | 5/347 |
| 3,855,635 | A | 12/1974 | Ramirez | 2/114 |
| 3,911,499 | A | 10/1975 | Benevento et al. | 2/114 |
| 3,950,789 | A | 4/1976 | Konz et al. | 2/93 |
| 4,055,173 | A | 10/1977 | Knab | 128/139 |
| 4,146,933 | A | 4/1979 | Jenkins et al. | 2/2 |
| 4,369,528 | A | 1/1983 | Vest et al. | 2/69 |

(Continued)

FOREIGN PATENT DOCUMENTS
FR    821150    11/1937
(Continued)

OTHER PUBLICATIONS

P.O. Fanger, Thermal Comfort: Analysis and Applications in Environmental Engineering, Danish Technical Press, 1970, pp. 5-67.

(Continued)

*Primary Examiner* — Roy Gibson
(74) *Attorney, Agent, or Firm* — Terrance A. Meador; INCAPLAW (57) ABSTRACT

A warming device includes a poncho-type patient gown having a major body portion with inside and outside surfaces, a central panel in the major body portion, opposing sleeve portions in the central panel, and a head opening in the central panel, between the sleeve portions. An inflatable convective warming apparatus is supported on a surface of the patient gown, extending from a lower edge of the patient gown at least to the head opening.

28 Claims, 9 Drawing Sheets

U.S. PATENT DOCUMENTS

| | | | | |
|---|---|---|---|---|
| 4,494,248 A | 1/1985 | Holder | | 2/69 |
| 4,524,463 A | 6/1985 | Ogden | | 2/105 |
| 4,558,468 A | 12/1985 | Landry et al. | | 2/51 |
| 4,578,825 A | 4/1986 | Vote | | 2/114 |
| 4,587,671 A | 5/1986 | Rodriguez et al. | | 2/69 |
| 4,651,727 A | 3/1987 | Howorth | | 128/201.3 |
| 4,653,120 A | 3/1987 | Leaf | | 2/114 |
| 4,696,066 A | 9/1987 | Ball et al. | | 2/272 |
| 4,718,124 A | 1/1988 | Sawicki et al. | | 2/114 |
| 4,787,101 A | 11/1988 | Feinberg | | 2/105 |
| 4,914,752 A | 4/1990 | Hinson et al. | | 2/2 |
| 4,964,282 A | 10/1990 | Wagner | | 62/259.3 |
| 5,062,424 A | 11/1991 | Hooker | | |
| 5,190,031 A | 3/1993 | Guibert et al. | | 128/399 |
| 5,255,390 A | 10/1993 | Gross et al. | | |
| 5,304,213 A | 4/1994 | Berke et al. | | 607/104 |
| 5,360,439 A | 11/1994 | Dickerhoff et al. | | 607/104 |
| 5,367,710 A | 11/1994 | Karmin | | 2/114 |
| 5,411,541 A | 5/1995 | Bell et al. | | 607/104 |
| 5,443,488 A | 8/1995 | Namenye et al. | | 607/104 |
| 5,572,742 A | 11/1996 | McFadden | | 2/114 |
| 5,575,006 A | 11/1996 | Wolfe | | 2/114 |
| 5,611,087 A | 3/1997 | Adkins | | 2/114 |
| 5,620,482 A | 4/1997 | Augustine et al. | | 607/107 |
| 5,697,963 A | 12/1997 | Augustine | | 607/108 |
| 5,733,318 A | 3/1998 | Augustine | | 607/104 |
| 5,749,109 A | 5/1998 | Kappel | | 5/423 |
| 5,768,707 A * | 6/1998 | Lederer | | 2/114 |
| 5,785,716 A | 7/1998 | Bayron | | 607/108 |
| 5,891,187 A | 4/1999 | Winthrop et al. | | 607/96 |
| 5,946,722 A | 9/1999 | Trautmann | | 2/83 |
| 5,970,519 A | 10/1999 | Weber | | 2/81 |
| 5,974,605 A | 11/1999 | Dickerhoff et al. | | 5/421 |
| 6,049,907 A | 4/2000 | Palomo | | 2/51 |
| 6,154,883 A | 12/2000 | Spann et al. | | 2/69 |
| 6,156,058 A | 12/2000 | Kappel et al. | | 607/107 |
| 6,203,567 B1 | 3/2001 | Augustine | | 607/104 |
| 6,216,270 B1 | 4/2001 | Moquin et al. | | 2/69 |
| 6,235,659 B1 | 5/2001 | McAmish et al. | | 442/79 |
| 6,378,136 B2 | 4/2002 | Matsushita | | 2/114 |
| 6,484,321 B1 | 11/2002 | Shamam | | 2/114 |
| 6,511,501 B1 | 1/2003 | Augustine et al. | | 607/96 |
| 6,524,332 B1 | 2/2003 | Augustine et al. | | 607/107 |
| 6,551,347 B1 | 4/2003 | Elkins | | 607/104 |
| 6,571,574 B1 | 6/2003 | Blackstone | | 62/420 |
| 6,596,019 B2 | 7/2003 | Turner et al. | | 607/108 |
| 6,647,552 B1 | 11/2003 | Hogan | | 2/114 |
| 6,694,522 B1 | 2/2004 | Neal | | 2/114 |
| 6,792,622 B2 | 9/2004 | Graves | | 2/114 |
| 6,799,332 B2 | 10/2004 | Hatton | | 2/114 |
| 6,820,622 B1 | 11/2004 | Teves et al. | | 128/849 |
| 6,851,125 B2 | 2/2005 | Fujikawa et al. | | 2/51 |
| 6,876,884 B2 | 4/2005 | Hansen et al. | | 607/98 |
| 7,001,416 B2 | 2/2006 | Augustine et al. | | 607/104 |
| 7,226,454 B2 | 6/2007 | Albrecht et al. | | 607/104 |
| 7,276,076 B2 | 10/2007 | Bieberich | | 607/108 |
| 7,364,584 B2 | 4/2008 | Anderson | | 607/108 |
| 7,470,280 B2 | 12/2008 | Bieberich | | 607/104 |
| 2003/0126668 A1 | 7/2003 | Scroggins | | 2/114 |
| 2005/0015127 A1 | 1/2005 | Bieberich | | 607/104 |
| 2005/0143796 A1 | 6/2005 | Augustine et al. | | 607/104 |
| 2006/0047332 A1 | 3/2006 | Malmberg et al. | | |
| 2006/0122671 A1 | 6/2006 | Albrecht et al. | | 607/104 |
| 2006/0122672 A1 | 6/2006 | Anderson | | 607/104 |
| 2006/0147320 A1 | 7/2006 | Hansen et al. | | 417/313 |
| 2006/0184216 A1 | 8/2006 | Van Duren | | 607/104 |
| 2006/0184217 A1 | 8/2006 | Van Duren | | 607/104 |
| 2006/0184218 A1 | 8/2006 | Bieberich | | 607/104 |
| 2006/0259104 A1 | 11/2006 | Panser | | 607/104 |
| 2007/0093882 A1 | 4/2007 | Anderson et al. | | 607/104 |
| 2007/0093883 A1 | 4/2007 | Anderson et al. | | 607/104 |
| 2007/0093884 A1 | 4/2007 | Anderson et al. | | 607/104 |
| 2007/0093885 A1 | 4/2007 | Anderson et al. | | 607/104 |
| 2007/0239239 A1 | 10/2007 | Albrecht et al. | | 607/96 |
| 2008/0027521 A1 | 1/2008 | Bieberich | | 607/96 |
| 2008/0027522 A1 | 1/2008 | Bieberich | | 607/96 |
| 2008/0125840 A1 | 5/2008 | Anderson | | 607/96 |
| 2008/0177361 A1 | 7/2008 | Anderson | | 607/108 |
| 2009/0062891 A1 | 3/2009 | Bieberich | | 607/104 |
| 2009/0149931 A9 | 6/2009 | Anderson | | 607/104 |
| 2009/0228083 A1 | 9/2009 | Anderson et al. | | 607/107 |

FOREIGN PATENT DOCUMENTS

| | | |
|---|---|---|
| GB | 475811 | 11/1937 |
| GB | 1 462 033 | 1/1997 |
| SE | 525 415 | 2/2005 |
| WO | WO 97/14381 | 4/1997 |
| WO | WO 98/48652 | 11/1998 |
| WO | WO 00/62726 | 10/2000 |
| WO | WO 03/086500 A2 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006/086587 A1 | 8/2006 |
| WO | WO 2007/047917 A1 | 4/2007 |
| WO | WO 2008/013603 | 1/2008 |
| WO | WO 2008/091486 | 7/2008 |

OTHER PUBLICATIONS

C.B. Mahony & J. Odom, Maintaining intraoperative normothermia: A meta-analysis of outcomes with costs. *AANA Journal*. Apr. 1999. v. 67, No. 2:155-164.

Porta-Chill—The Portable Air-Chiller—Brochure, http://www.portachil.com/, Dec. 3, 2002.

EPO Examination Report mailed Oct. 24, 2006, in EPO3719690.4-1526, EP Regional Phase of PCT/US2003/11128 (published as WO/2003/086500).

EPO Examination Report mailed Dec. 17, 2007, in EPO3719690.4-1526, EP Regional Phase of PCT/US2003/11128 (published as WO/2003/086500).

EPO Examination Report mailed Sep. 2, 2008, in EP05789978.3, EP Regional Phase of PCT/US2005/025355 (published as WO/2006/020170).

EPO Examination Report mailed Jan. 23, 2009, in EP05853202, EP Regional Phase of PCT/US2005/044214 (published as WO/2006/063027).

EPO Examination Report mailed Sep. 29, 2009, in EP06720577.3.

EPO Examination Report mailed Apr. 24, 2009, in EP06826351.6.

EPO Examination Report mailed Jun. 22, 2009, in EP05853202.9.

International Search Report and Written Opinion in PCT/US2005/025355, mailed Dec. 1, 2005.

International Search Report and Written Opinion in PCT/US2005/043968, mailed Apr. 19, 2006.

International Search Report and Written Opinion in PCT/US2005/044214, mailed Apr. 19, 2006.

International Search Report and Written Opinion in PCT/US2006/004644, mailed Dec. 18, 2006.

International Search Report and Written Opinion in PCT/US2006/041028, mailed Feb. 20, 2007.

International Search Report and Written Opinion in PCT/US2007/013073, mailed Nov. 9, 2007.

International Search Report and Written Opinion in PCT/US2008/000141, mailed Nov. 11, 2008.

* cited by examiner

WARMING DEVICE CONSTRUCTIONS WITH A PONCHO-TYPE PATIENT GOWN

PRIORITY AND RELATED APPLICATIONS

This Application claims priority as a continuation-in-part of U.S. Ser. No. 10/508,319, filed Mar. 3, 2005, now U.S. Pat. No. 7,837,721, which is a 371 of PCT/US03/11128, filed Apr. 10, 2003, which claims the benefit of 60/371,314, filed Apr. 10, 2002.

This application contains subject matter related to the subject matter of the following patent applications, all commonly owned herewith:

Patent Cooperation Treaty (PCT) Application No. PCT/US03/11128, filed Apr. 10, 2003, entitled "Patient Comfort Apparatus and System", and published on Oct. 23, 2003 under Publication No. WO 2003/086500;

Patent Cooperation Treaty (PCT) Application No. PCT/US05/025355, filed Jul. 18, 2005, entitled "Perioperative Warming Device", and published on Feb. 23, 2006 under Publication No. WO 2006/020170;

Patent Cooperation Treaty (PCT) Application No. PCT/US05/043968, filed Dec. 6, 2005, entitled "Warming Device with Varied Permeability", and published on Jun. 15, 2006 under Publication No. WO 2006/062910;

Patent Cooperation Treaty (PCT) Application No. PCT/US05/044214, filed Dec. 6, 2005, entitled "Warming Device", and published on Jun. 15, 2006 under Publication No. WO 2006/063027;

Patent Cooperation Treaty (PCT) Application No. PCT/US06/004644, filed Feb. 9, 2006, entitled "Warming Device for Perioperative Use", and published on Aug. 17, 2006 under Publication No. WO 2006/086587;

U.S. patent application Ser. No. 10/411,865, filed Apr. 10, 2003, entitled "Patient Comfort Apparatus and System" and published on Oct. 16, 2003 under Publication No. US 2003/0195596 and issued on Feb. 21, 2006 under U.S. Pat. No. 7,001,416;

U.S. patent application Ser. No. 10/508,319, filed Sep. 20, 2004, entitled "Patient Comfort Apparatus and System" and published on Jun. 30, 2005 under Publication No. US 2005/0143796;

U.S. patent application Ser. No. 11/005,883, filed Dec. 7, 2004, entitled "Warming Device with Varied Permeability" and published on Jun. 8, 2006 under Publication No US 2006/0122671;

U.S. patent application Ser. No. 11/006,491, filed Dec. 7, 2004, entitled "Warming Device" and published on Jun. 8, 2006 under Publication No. US 2006/0122672;

U.S. patent application Ser. No. 11/057,396, filed Feb. 11, 2005, entitled "Perioperative Warming Device", and published on Aug. 17, 2006 under Publication No. US 2006/0184215;

U.S. patent application Ser. No. 11/057,403, filed Feb. 11, 2005, entitled "Warming Device for Perioperative Use", and published on Aug. 17, 2006 under Publication No. US 2006/0184217;

U.S. patent application Ser. No. 11/057,404, filed Feb. 11, 2005, entitled "Clinical Garment for Comfort Warming and Prewarming", and published on Aug. 17, 2006 under Publication No. US 2006/0184218; and, U.S. patent application Ser. No. 11/363,136, filed Feb. 27, 2006, entitled "Forced Air Warming Unit" and published on Jul. 6, 2006 under Publication No. US2006/0147320.

BACKGROUND

A device for warming a patient in a clinical environment includes a poncho-type patient gown with an inflatable convective warming apparatus supported on the patient gown.

Inflatable thermal blankets that transfer heat to a human body by convection are known. In this regard, an inflatable thermal blanket receives a stream of pressurized, warmed air, inflates in response to the pressurized air, distributes the warmed air within a pneumatic structure, and emits the warmed air onto a body to accomplish such objectives as increasing comfort, reducing shivering, and treating or preventing hypothermia. Arizant Healthcare Inc., the assignee of this application, sells such inflatable thermal blankets under the BAIR HUGGER® brand.

Figure 1A:
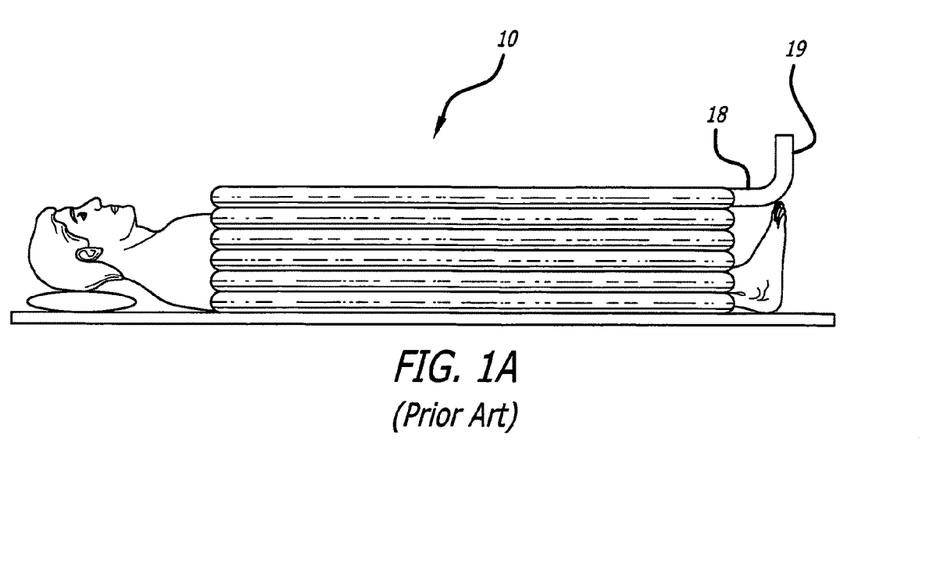
FIGS. 1A-1D are illustrations of prior art full body, lower body, and upper body convective thermal blankets.
Figure 1B:
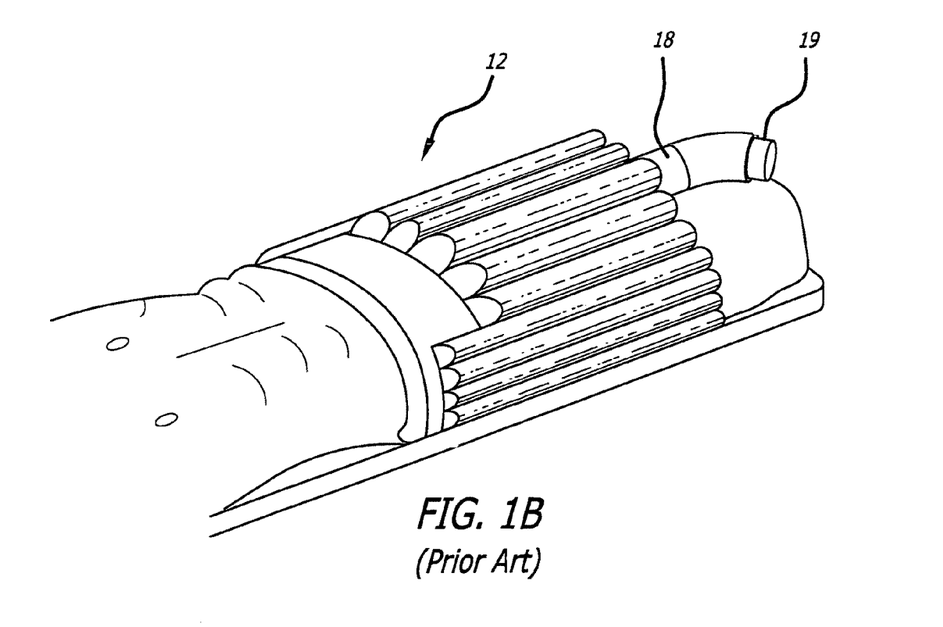
Figure 1C:
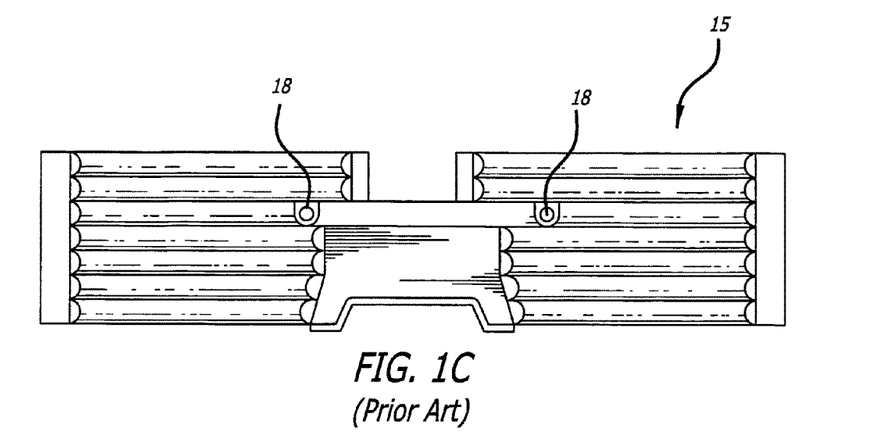
Figure 1D:
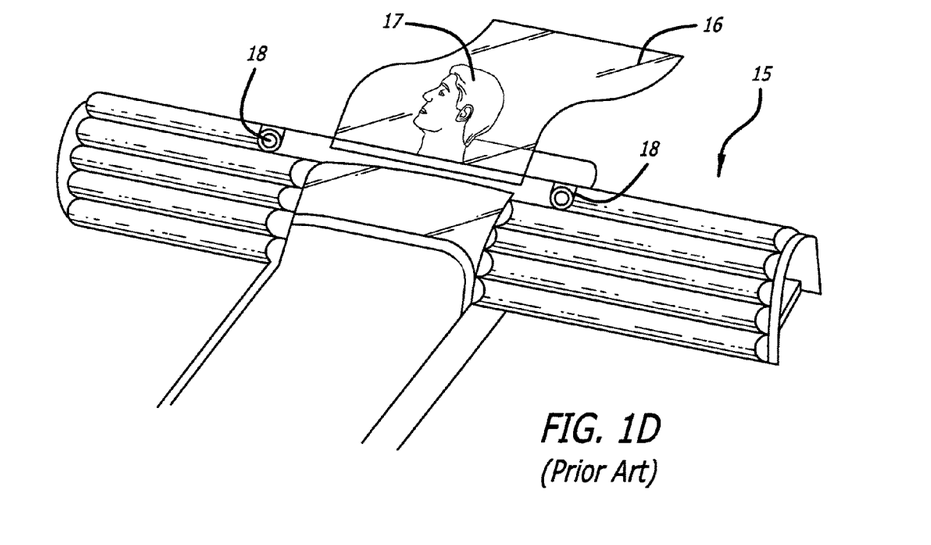

Inflatable thermal blankets have been specifically designed for particular deployments where therapeutic warming is indicated. Three representative inflatable thermal blankets known in the prior art are shown in FIGS. 1A-1D. A "full body" inflatable thermal blanket 10 is shown in FIG. 1A. The full body blanket 10 is adapted to lie upon a patient and to extend longitudinally along the body of the patient in order to cover substantially the patient's entire body, from near the ankles or feet up to the neck. A "lower body" thermal blanket 12 shown in FIG. 1B is adapted to lie upon a patient and to extend longitudinally along the body in order to cover the patient's lower body, from near the ankles or feet up to the waist or pelvis. An "upper body" thermal blanket 15 is illustrated in FIGS. 1C and 1D. When fed a stream of warmed pressurized air, each of the thermal blankets 10, 12, 15 inflates and distributes the air within itself. While the thermal blanket lies on the patient, the warmed pressurized air flows through apertures or interstices in a permeable surface of the thermal blanket which faces the patient. These thermal blankets may have one, two, or more inlet ports 18 through which an air hose 19 provides warmed pressurized air from a heater/blower unit (not shown in these drawings).

The construction of these prior art inflatable thermal blankets is well understood. Examples of specific constructions are given in U.S. Pat. Nos. 5,620,482, 5,443,488, 5,360,439, and 5,304,213. See also U.S. Pat. No. 5,974,605.

The inflatable thermal blankets of FIGS. 1A-1D have a narrow range of clinical application; they are designed and constructed to function during the intra- and post-operative periods upon prone patients. They cannot be used preoperatively on an upright or standing patient without provision for being supported on the patient's body. Moreover, if deployed and operated vertically with respect to a standing or sitting patient, much of the warmed air emitted by a thermal blanket is lost because the blanket cannot be draped around the patient.

A novel device which solves the problem of warming patients that may be standing, sitting, or prone is disclosed in the referenced Patent Application Publication No. US 2005/0143796, which is incorporated herein by reference. This warming device includes a clinical garment which is adapted to support an inflatable convective warming apparatus in order to warm a person wearing the clinical garment, thereby providing for the person's comfort without limiting the person's mobility. A novel multifunction warming device for perioperative use described in the referenced Patent Application Publication No. US 2006/0122671, which is incorporated herein by reference. This multifunction warming device is constituted of a clinical garment and an inflatable convective warming apparatus constructed for comfort warming and/or therapeutic warming that is supported on a surface of the clinical garment.

Patient warming devices manufactured and sold by Arizant Healthcare Inc. under the BAIR PAWS® brand include a clinical garment and one or more inflatable convective warming apparatuses supported on one or more surfaces of the garment. Constructions of these patient warming devices are disclosed in detail in the published patent applications and issued patents referenced in paragraph [0002]. While a patient wears the clinical garment, a convective warming apparatus supported on an inside surface of the garment is inflated with a stream of warmed, pressurized air and emits the warmed air within the garment to provide comfort warming during the preoperative phase. The patient warming device is deployed on the patient and operated to provide therapeutic warming during and after surgery. The clinical garment is a sleeved, robe-like garment, made of a soft, non-woven material. It has a back or side opening that is closed by ties. The sleeves, which are sewn on to the clinical garment after a body of the garment is formed, can be opened and closed again along their upper seams to provide access to the upper arms and chest of the patient wearing the garment. The garment can be opened, removed from, and repositioned on the patient during and after surgery to provide upper, full, or lower body therapeutic warming. This construction provides clinically effective warming solutions for all periods of the perioperative cycle.

The efficacy of warming a patient for comfort preoperatively and then warming a patient for therapy during, and after surgery has been well documented. (Yilmaz M, et al. Impact of perioperative warming on maintenance of normothermia and outcome after colorectal surgery. *Anestheseology* 2008; 109: A880-A881). The assignee's BAIR PAWS products effectively provide both comfort and therapeutic warming throughout the perioperative cycle. (Wagner D, et al. Effects of comfort warming on preoperative patients. *AORN* 2006; 84: 427-448. Andrzejowski J, et al. Effect of prewarming on post-induction core temperature and the incidence of inadvertent perioperative hypothermia in patients undergoing general anaesthesia. *BJA* 2008; 101, 5: 627-631).

Nevertheless, there are needs for alternate patient warming device constructions that provide new garment configurations with additional modes of patient access, simplified manufacturing, and alternate means of deployment during intra-operative use.

These needs are met with a patient warming device that includes a patient gown with a poncho-type construction and at least one inflatable convective warming device supported on a surface of the patient gown. The poncho-type construction provides access to both sides of a patient through opposing side openings that can be opened and closed. Additionally, a poncho-type construction with sleeves provides access to the upper chest and arms of the patient through both upper and lower portions of the sleeves. The poncho-type construction is particularly suited to simple, inexpensive modes of manufacture in which sleeves are provided by cutting a web of patient gown material instead of by attachment of sleeve portions during or after web processing. Furthermore, the poncho-type construction provides a multi-mode patient warming device with an easily-manipulated patient gown that does not need to be removed or detached from the patient to provide a particular mode of therapeutic warming.

SUMMARY

A warming device includes a patient gown having a suitable opening, such as a head opening in a poncho-type gown. Preferably, the patient gown is a poncho-type gown having front and rear panels, and a central panel between the front and rear panels, in which a head opening is provided in the central panel to admit the head. An inflatable convective warming apparatus is supported on a surface of the patient gown.

Preferably, the inflatable convective warming apparatus is supported on an inside surface of the patient gown, substantially in the front section, extending from the head opening toward a lower edge of the front section.

In some embodiments, the inflatable convective warming apparatus extends on the inside surface, along the front and rear panels, and includes a head opening aligned with the patient gown head opening.

In some embodiments, the inflatable convective warming apparatus includes separately inflatable sections designed to provide different modes of patient warming. Each section is capable of being inflated by a distinct heater/blower apparatus designed to provide an air stream conditioned for a particular mode of patient warming. Alternately, each section is capable of being inflated by a heater/blower unit designed to selectively provide respective air streams conditioned for particular modes of patient warming.

The poncho-type patient gown is made from an essentially rectangular blank of material, which supports convenient, simple, and inexpensive mass production of the warming device on a web-based manufacturing line.

In some embodiments, a patient warming device in which at least one mode of patient warming is provided by an inflatable convective warming apparatus supported on a poncho-type patient gown is deployed in the same manner as an upper body thermal blanket by rotating the poncho-type patient garment about the patient's neck to position the inflatable convective warming apparatus across the patient's arms when the patient is supine.

DETAILED DESCRIPTION OF THE PREFERRED EMBODIMENTS

In the patient warming device illustrated, described, and claimed below a "patient gown" is a garment made of a lightweight, soft, flexible material that is used to clothe a patient in a clinic, hospital, or other medical or dental facility when undergoing examination or treatment by medical or dental personnel. This definition excludes clothes and other garments intended for daily wear and which a patient is typically directed to remove before putting on a patient gown. Such clothes and other garments including, without limitation, shirts, coats, overcoats, bibs, vests, sweaters, trousers, dresses, and any and all equivalent garments.

In the patient warming device illustrated, described, and claimed below, a convective warming apparatus is "inflatable". That is, its structure, flaccid when not in use, tautens, distends, swells, and/or dilates in response to receipt of a stream of pressurized air. However, it should be noted that the term "inflatable" when used in this description and the claims below signifies a potential, but not necessarily an actual state of inflation.

In the patient warming device illustrated, described, and claimed below, the term "convective" denotes a mechanism for transferring heat from an inflatable warming apparatus to a body by air emitted from the apparatus. In this regard, the term refers to the principal heat transfer mechanism, it being understood that heat can also be transferred from the apparatus to the body by conduction and/or radiation, although not to the degree of convection.

A patient warming device is constructed to provide comfort warming and/or therapeutic warming to a patient. In this regard, a patient warming device including a patient gown having the construction of a poncho, with at least one convective warming apparatus supported on a gown surface, is releasably closed on both sides and worn with an open bottom by an ambulatory patient for comfort warming. For therapeutic warming, the poncho-type patient gown is opened and rotated to be deployed on a prone or supine patient in the manner of an upper, lower, or full body inflatable thermal blanket.

Figure 2:
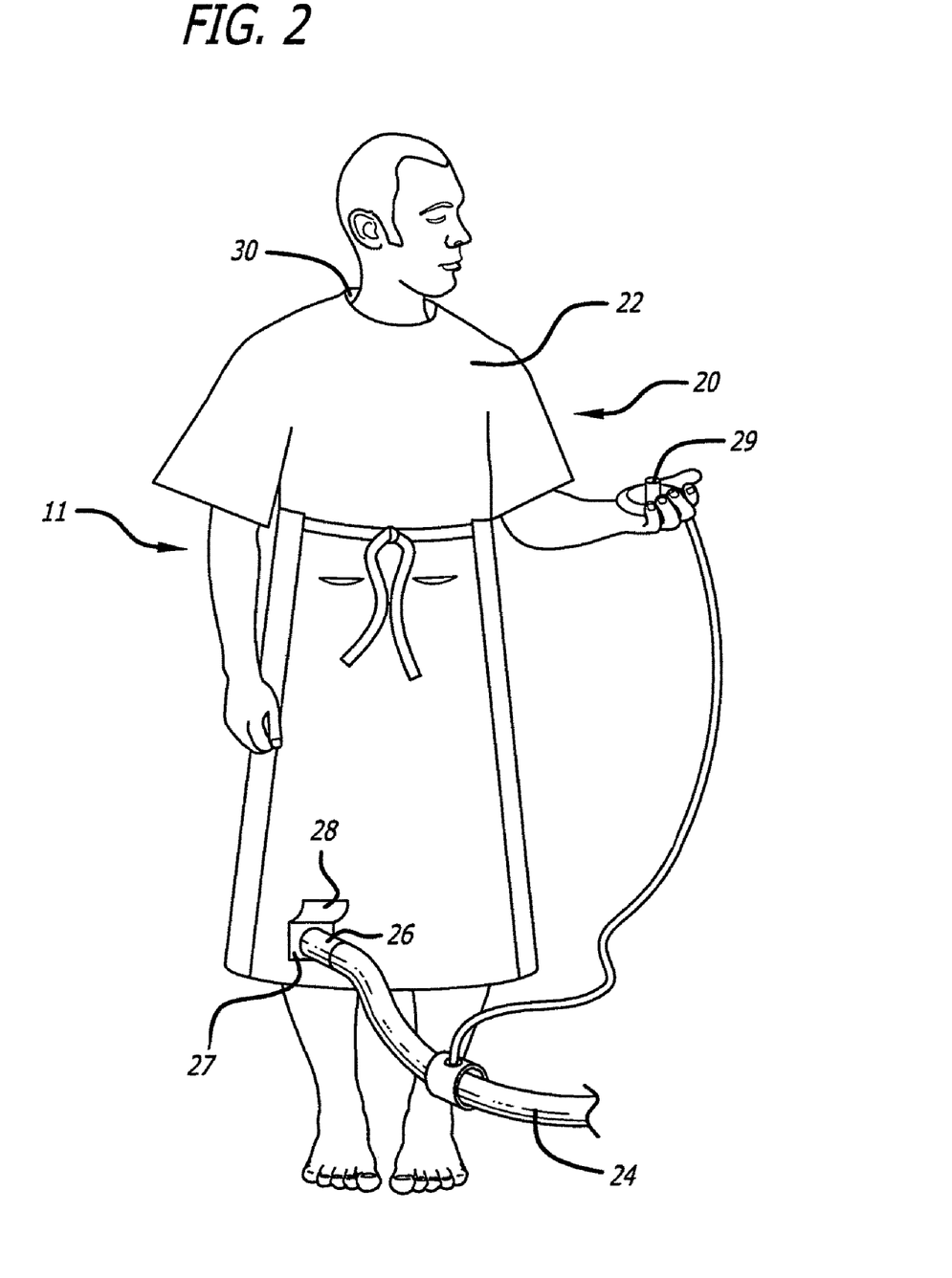
FIG. 2 is an illustration of a patient wearing a warming device including a poncho-type patient gown with an inflatable convective warming apparatus supported on an inside gown surface.

In FIG. 2, a patient 11 is wearing a patient warming device 20. The patient warming device 20 is constituted of a patient gown 22 and one or more inflatable convective warming apparatuses (not seen in this view) that are supported on an inside surface of the patient gown 22. Such an inflatable convective warming apparatus (hereinafter "convective warming apparatus") is operated in response to a stream of warmed, pressurized air provided from a heater/blower unit (not seen in this view) through an air hose with an outlet end (preferably, but not necessarily, a nozzle) that is received in an inlet port of the convective warming apparatus. One such air hose 24, with a nozzle 26, is shown in FIG. 2. One such inlet port is indicated by reference numeral 27 in FIG. 2. Preferably, the inlet port 27 is accessed through an opening 28 in the patient gown 22. Optionally, but not necessarily, a manually-operated control device 29 is provided for operation by the patient to modulate operation of the heater/blower unit (not shown) during comfort warming. For example, the control device 29 permits the patient to adjust either or both of temperature and velocity of a stream of warmed, pressurized air inflating a convective warming apparatus constructed to deliver comfort warming to the patient. In this regard, see, for example, the forced air warming unit described in related Publication No. US2006/0147320.

Figure 3A:
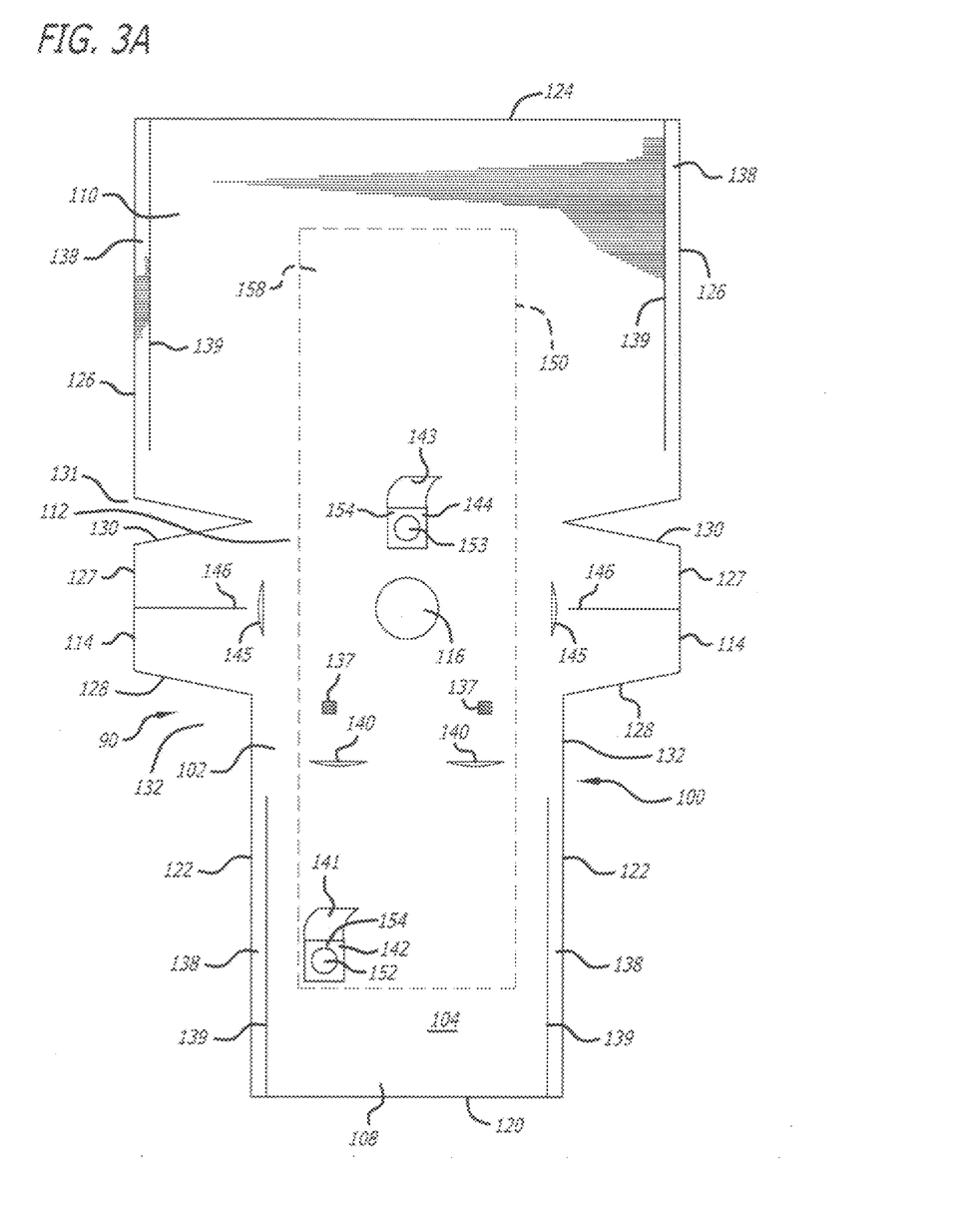
FIGS. 3A and 3B are, respectively, outside and inside plan views of a preferred embodiment of a warming device including a poncho-type patient gown opened in a longitudinal direction and an inflatable convective warming apparatus supported on an inside surface of the gown.
Figure 3B:
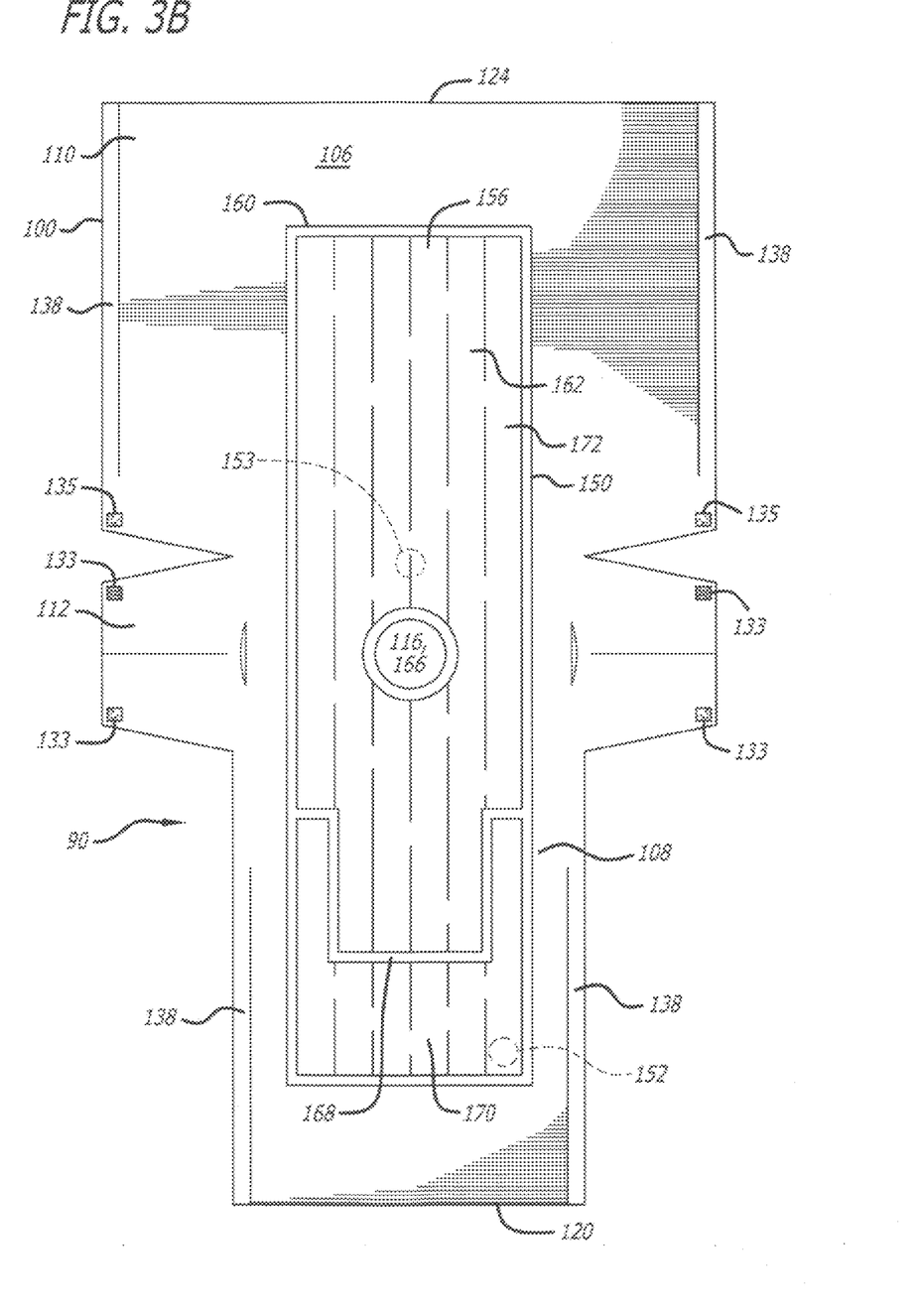

The patient gown 22 of FIG. 2 has a poncho-type configuration in the form of a blanket-like cloak with an opening 30 in the center to receive the head. As shown in FIG. 2, when assembled so as to be worn by the patient, the poncho-type configuration of the patient gown 22 is supported primarily at the shoulders and/or neck of a patient, with the patient's head received in the head opening 30 and respective panels of the patient gown draped vertically from the head opening down the front and back sides of the patient. The poncho-type construction affords mobility for the patient, and also provides convenience for the clinician during examination because it can be easily opened, moved, adjusted, and removed and put back on. As will be described with respect to FIGS. 5 and 6, during and after surgery, the poncho-type configuration can be opened so that the patient gown can be spread out and deployed on a patient with a convective warming apparatus facing the patient; in this case, the patient gown can be draped over and/or around the patient. In any mode of heating, the at least one convective warming apparatus receives a stream of warmed pressurized air, inflates, and emits the warmed air through one or more permeable surfaces to warm the patient's body FIGS. 3A and 3B illustrate elements of a preferred patient gown construction in a patient warming device in which at least one mode of patient warming is provided by a convective warming apparatus supported on the inside surface of a poncho-type patient gown. The possible modes of patient warming include at least comfort warming and therapeutic warming. In these figures, the patient gown is opened and laid flat to illustrate an outside surface (FIG. 3A) and an inside surface (FIG. 3B). As per these figures, a patient warming device 90 includes a patient gown 100 having a major body portion 102 with outside and inside surfaces 104 and 106, front and back panels 108 and 110, a central panel 112 joining the front and back panels, sleeve portions 114 on opposing sides of the central panel, and a head opening 116 in the central panel, between the sleeve portions. The periphery of the front panel 108 includes a lower edge 120 and opposing side edges 122. The periphery of the back panel includes a lower edge 124 and opposing side edges 126. The sleeve portions include side edges 127, front edges 128, and back edges 130. Darts 131 are cut into the opposing edges of the major body portion 102 between the back and central panels 110 and 112. The opposing side edges 122 of the front panel are defined by opposing notches 132 cut into the opposing edges of the major body portion 102 so that the width of the front panel 108 is less than the width of the back panel 110. Thus, the front panel 108 is narrower than the back panel 110.

With reference to FIG. 3B, the patient gown 100 is assembled into the poncho-type configuration shown in FIG. 2 by folding the major body portion 102 in the central portion 112 so as to bring the front and back panels 108 and 110 in opposed alignment, with the inside surface 106 enclosed therebetween. The front and back edges 128 and 130 of each sleeve portion 114 are brought together to form sleeves with lower seams that are releasably attached by means 133 located and acting between those edges. Such means include, for example, buttons, snaps, hook and loop material, tape, and/or straps, or any equivalent thereof. Such means are operable to allow full or partial separation of the front and back edges 128 and 130, and to again attach these edges, once separated.

The patient gown 100 is releasably closed along its sides by bringing the inside surface 106 along the opposing side edges 126 in the back panel 110 over the outside surface along the opposing side edges 122 of the front panel 108. Means 135 seen in FIG. 3B are provided on the inside surface 106 at the intersection of each of the opposing side edges 126 of the back panel 110 and the side of a dart 131. Means 137 seen in FIG. 3A are provided on a portion of the outside surface 104 on the front panel 108 and interact with the means 135 to releasably attach the back and front panels. The means 135 and 137 include, for example, buttons, snaps, hook and loop material, and/or tape, or any equivalent thereof. Such means are operable to allow full or partial separation of the sides of the patient gown 100, and to again attach these sides, once separated. Optionally, tie straps are provided to be tied together around the outside of the patient gown 100, near its middle, in order to close the sides of and/or cinch the patient gown 100 about the patient. The tie straps may be attached to the patient gown 100, or formed integrally therewith as a step in manufacturing the patient gown 100. For example, two sets of integrally-formed opposing tie straps 138 are seen in FIGS. 3A and 3B, one set formed in the front panel 108 just inside the opposing side edges 122, and the other formed in the back panel 110 just inside the opposing side edges 126. Optionally, each tie strap is detachably attached, by a line of perforations 139, to the side edge in which it is formed.

Preferably, the patient gown 100 is constructed from lightweight, soft, flexible nonwoven or woven materials. For example, we have made a patient gown with a poncho-type construction from a non-woven blend of spunlace polyester and wood pulp. Another material from which patient gowns can be made is a non-woven blend of spunlace polypropylene and wood pulp.

In FIG. 3A, optional hand slits 140 are cut through the patient gown 100. Optional flaps 141 and 143 are formed in the patient gown to cover openings 142 and 144. Preferably the opening 142 is positioned in the front panel 108 near a side edge 122, and the opening 144 is positioned in the back panel 110. Optionally, the opening 142 is centered between the apices of the darts 131, below the head opening 116. Optional elongate longitudinal slits 145 and/or transverse perforation lines 146 may be provided in the central panel 112, substantially centered in each sleeve portion 114 so that access may be provided to either or both of a patient's arms and chest for placement of instruments, insertion of stents, examination, and so on without having to remove the patient gown from the patient's neck.

With further reference to FIGS. 3A and 3B, an alternate patient gown embodiment has no notches formed between the front and central panels 110, 112, in which case the front and back panels 110, 108 have the same width. In this embodiment, another set of opposing darts is cut between the central and front panels to define the sleeve portions 114. This alternate embodiment of the patient gown does have more bulk than the embodiment with notches 132; however, it results in less wastage of the gown material during manufacturing.

As illustrated in FIGS. 3A and 3B, there is at least one inflatable convective warming apparatus 150 supported on the inside surface 106 of the patient gown 100 along the front and central panels at least to the head opening. The convective warming apparatus 150 includes at least one inlet port 152 into an area 154 of the convective warming apparatus 150. The inlet port is constructed to receive and retain the end of an air hose which delivers a stream of warmed pressurized air to operate the convective apparatus 150. The convective warming apparatus 150 includes a relatively gas-permeable sheet 156 of material attached to a relatively gas-impermeable sheet of material 158 by a peripheral seal 160 between the peripheries of the sheets 156 and 158. An inflatable space is thereby defined between the sheets 156 and 158. Preferably, the peripheral seal 160 is continuous; optionally, openings may be provided in the peripheral seal 160 to vent pressurized air from the inflatable space in order to reduce variations in the temperature of inflating air across the inflatable space. Within the peripheral seal 160, the sheets are sealed together at stake points 162 or discontinuous elongate seals (not shown). A stream of pressurized, warmed air flowing through an inlet port causes the inflatable space to inflate. The warmed pressurized air is distributed in the inflatable space. The stake points or discontinuous seals keep the inflatable space from ballooning when inflated and also establish patterns of air circulation designed to reduce temperature variations across the inflatable space, and to avoid interruption of air movement. Air pressure builds in the inflatable space in response to the stream of pressurized, warmed air, causing warmed air to circulate and be emitted from the inflatable space through the relatively gas-permeable sheet 156.

An optional construction of the convective apparatus 150 includes one or more continuous seals that define features of the apparatus. In this regard, as per FIGS. 3A and 3B, a continuous head opening seal 164 between the sheets 156 and 158 surrounds a head opening 166 in the convective warming apparatus 150. A generally U-shaped continuous seal 168 between the sheets 156 and 158 partitions the convective warming apparatus into first and second separately-inflatable sections 170 and 172, each with at least one inlet port 152 and 153, respectively. In this optional construction, the first section 170, constructed for comfort warming, has a generally U-shaped outline with an elongate base in a spaced parallel relationship with the lower edge 120 of the front panel 108. The second section 172, constructed for therapeutic warming, has an elongate rectangular configuration, one end of which narrows to fit into the notch formed between the arms of the first section's U-shape. The second section extends along the inside surface 106, over the central and back panels 112 and 110, with its second end disposed in a spaced parallel relationship with the lower edge 120 of the front panel 108. As seen in FIGS. 3A and 3B, the head opening 166 is located in the second section 172.

As per FIGS. 3A and 3B, when convective warming apparatus 150 is positioned on the inside surface 106, the head opening 166 is aligned with the head opening 116, the inlet port 152 is positioned so as to be accessible through the opening 142, and the inlet port 153 is positioned so as to be accessible through the opening 144. Further, the locations of the hand slits 140 in the front panel 108 of the gown enable a patient to insert her or his hands into the patient gown 100, so as to be warmed between the inside surface 106 and the inflatable convective warming apparatus 150.

As can be seen in FIGS. 3A and 3B, the convective warming apparatus 150 is preferably positioned so as to provide comfort warming inside the patient gown, in the front portion thereof. For example, the optional construction of the inflatable convective warming apparatus 150 places the first section 170 in a lower portion of the front panel 108, with the gas-permeable sheet 156 facing inwardly of the patient gown 100. In this position, the air emitted for comfort warming is directed to the front of a patient wearing the warming device as shown in FIG. 2. For example, the U-shaped configuration of the first section 170 emits air for comfort warming across a patient's shins through its base and along the front surfaces of the patient's thighs, toward the patient's groin and lower abdomen, through its arms.

In the optional construction of the inflatable convective warming apparatus shown in FIGS. 3A and 3B, both sections 170 and 172 share the gas-permeable and gas-impermeable sheets 156 and 158. However, the structure of the first section 170 is designed to deliver comfort warming, while the structure of the second section 172 is designed to deliver therapeutic warming. In this regard, the portion of the gas-permeable sheet 156 incorporated into the first section 170 has a lower average permeability than the portion of the gas-permeable sheet 156 incorporated into the second section 172. Further, the volume of the inflatable space in the first section 170 is less than in the second section 172. The lower average permeability of the section 170 accommodates a lower air pressure entering the first section 170, causing warmed air to be emitted at a lower velocity than the second section. The smaller volume of the first section also delivers less total heat per unit of time than the larger volume of the second section.

The inflatable convective apparatus embodiment shown in FIGS. 3A and 3B can be constructed for operation with separate heater/blower units having different capacities. For example, the first section 170 can be operated with a low capacity heater/blower unit located in an examination room or a pre-operative waiting area which is capable of delivering a stream of air in temperature/velocity combinations appropriate for comfort heating, while the second section 172 can be operated with a higher capacity heater/blower unit located in a surgery or a PACU which is capable of delivering a stream of air in temperature/velocity combinations appropriate for therapeutic heating. Alternately, each of the first and second sections 170 and 172 can be operated by heater/blower units at any location which are capable of delivering a stream of air at selectable or adjustable combinations of temperature and velocity. Further, with careful selection of volume, permeability, and air circulation structure, some inflatable convective warming apparatus constructions could provide distinct comfort and therapeutic modes of warming without dividing the convective warming apparatus into separately-inflatable sections. In such a case, the convective warming apparatus would be inflated at a lower pressure for comfort warming than for therapeutic warming, and would exhibit some degree of flaccidness during comfort warming operation. Manifestly, the inflatable convective warming apparatus can also be constructed for a single patient warming mode. For example, the convective warming apparatus can be constructed for either comfort warming or therapeutic warming. Also, two or more separate inflatable convective warming apparatuses can be supported on the patient gown, one constructed to provide one mode of patient warming, such as comfort warming, and another to provide a second mode of patient warming, for example, therapeutic warming.

Figure 4A:
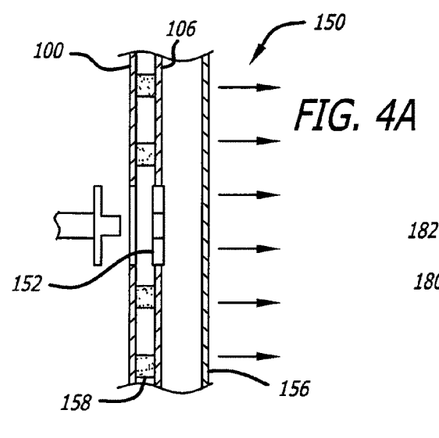
FIG. 4A is a side sectional, partially schematic, drawing showing construction details of a first preferred construction of a warming device including a poncho-type patient gown with an inflatable convective warming apparatus supported on an inside surface of the gown.

Thus, as per FIG. 4A, an inflatable convective warming apparatus 150 is made by joining two sheets of material with a closed impermeable seal running between the sheets, along their peripheries. One or more additional impermeable seals are provided to define elements such as a head opening. One sheet 156 is relatively gas-permeable to permit airflow therethrough, and the other sheet 158 is relatively gas-impermeable so as to prevent airflow therethrough. The two sheets are further connected by discontinuous seals or stake points within the peripheral seals; the two sheets may be separate from the patient gown 100, in which case a convective warming apparatus is permanently or releasably attached, fixed, or mounted or adhered to either the outside or inside surfaces of the patient gown 100. The inlet port 152 or inlet ports 152, 153 are formed in or mounted to the convective warming apparatus, and are preferably located in at least a portion of the gas-impermeable sheet.

Figure 4B:
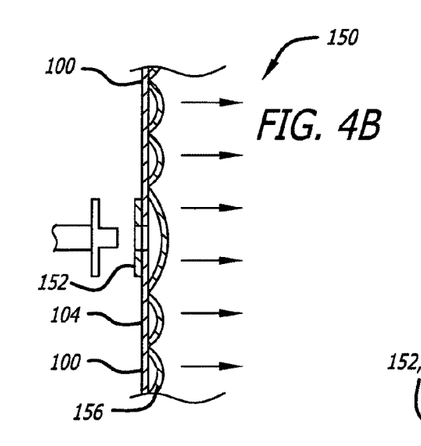
FIG. 4B is a side sectional, partially schematic, drawing showing construction details of a second preferred construction of a warming device including a poncho-type patient gown with an inflatable convective warming apparatus supported on an inside surface of the gown.

As per FIG. 4B, in other cases, the gas-permeable sheet 156 can be sealed to a portion of the inside surface 106 of the patient gown 100 to form the convective warming apparatus 150. In these other cases, at least the portion of the patient gown 100 to which the gas-permeable sheet 156 is attached is either inherently gas-impermeable, or is constructed to be so, and the inlet port 152 or inlet ports 152, 153 are formed on or mounted to the outside surface 104 of the patient gown. Optionally, the gown material can be somewhat gas-permeable, although to a lesser degree than the gas-permeable sheet. In these cases, since the gas-permeable sheet is supported on the inside surface of the patient gown, the convective warming apparatus 150 is supported, at least in part, on the inside surface 106.

Figure 4C:
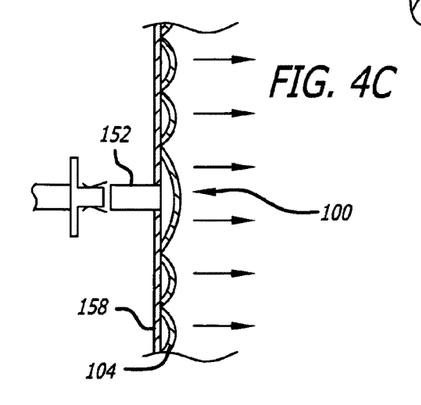
FIG. 4C is a side sectional, partially schematic, drawing showing construction details of a third preferred construction of a warming device including a poncho-type patient gown with an inflatable convective warming apparatus supported on an inside surface of the gown.

As per FIG. 4C, if at least a portion of the patient gown 100 is relatively gas-permeable, a gas-impermeable sheet 158 can be sealed to the outside surface 104 of the patient gown 100, over the gas-permeable portion of the patient gown. In these cases, the inlet port 152 or inlet ports 152, 153 are formed on or mounted to the gas-impermeable sheet 158 mounted to the outside surface 104 of the patient gown 100. Further, since the gas-permeable potion of the patient gown 100 includes a portion of the inside surface 106 of the patient gown, the convective warming apparatus 150 is supported, at least in part, by remaining portions of the inside surface 106.

In all of these cases, the convective warming apparatus is supported on the patient gown in such a manner that the gas-permeable sheet emits warmed air inwardly of the patient gown 100, when the gown is worn or deployed with the inside surface 106 facing, if not surrounding, the patient.

Figure 5A:
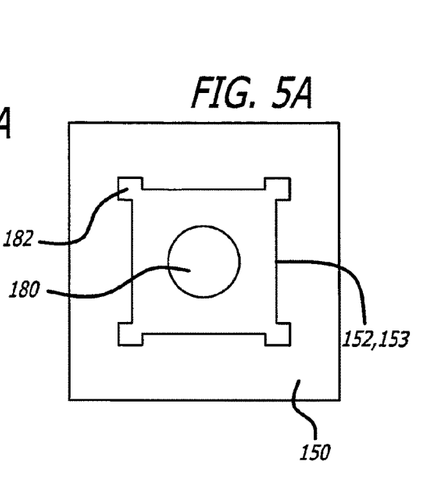
FIGS. 5A and 5B are, respectively, illustrations of inlet port embodiments.
Figure 5B:
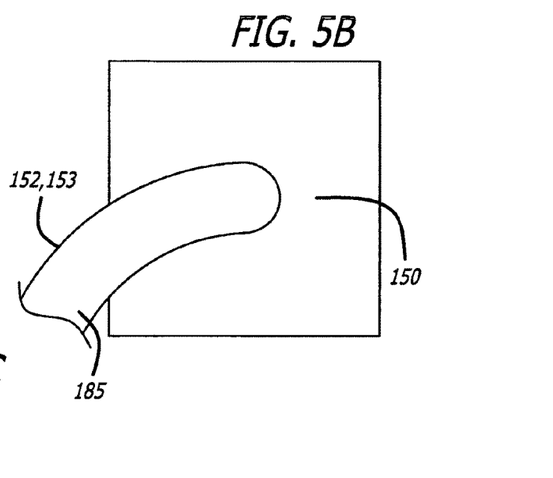

In some cases, as seen in FIG. 5A, an inlet port 152, 153 is constituted of an opening 180 through at least a portion of the convective warming apparatus 150. In a preferred embodiment, the opening 180 is a generally circular hole that is surrounded by a collar 182 of somewhat flexible material, such as cardboard or plastic. The hole 180 can be made fully open during manufacturing by removal of material of the convective warming apparatus through which the hole 180 opens. Alternatively, the hole 180 can be initially defined during manufacturing by perforations of any pattern in material of the convective warming apparatus, and then fully opened when the nozzle of an air hose is pushed through it. Further, an inlet port according to FIG. 5A can be provided with a removable plug as in constructions where two or more inlet ports are provided in either or both sections of the convective warming device. Examples of such an inlet port are described and illustrated in U.S. Pat. No. 7,578,837. In other cases, as seen in FIG. 5B, an inlet port 152, 153 includes a sleeve or tube 185 of flexible material that opens through the convective warming apparatus 150 into the inflatable space. Examples of such inlet ports are described in Publication No. WO 2003/086500 and are illustrated in U.S. Pat. No. 5,360, 439.

According to the present best mode of construction of the convective warming device, a single inflatable convective warming apparatus with separately inflatable sections is fabricated or assembled separately from the patient gown and then attached to its inside surface by sewing, gluing, heat sealing, or welding, or any combination of these. The convective warming apparatus is formed by heat sealing two sheets of material together. The relatively gas-permeable sheet is a laminate sheet comprising a layer of nonwoven material on which a layer of polypropylene is extruded, and the gas-impermeable sheet is a polypropylene film. Apertures are formed through the laminate sheet to make it permeable; and permeability is established by the size and density of the apertures. The polypropylene film and the polypropylene layer are sealed together along their peripheries to form inflatable space and within their peripheries at discontinuous seals or stake points. Other seals are made between the polypropylene film and the polypropylene layer to form separate sections and other features, as required. The polypropylene film (of which the gas-impermeable sheet is constituted) is attached by gluing, sewing, or heat sealing to the inside surface of the patient gown and the nonwoven material layer of the gas-permeable sheet faces the patient. The reason for locating the polypropylene film on the inside surface of the patient gown is to reduce the bulk and stiffness of the inflatable convective warming apparatus, thus making the warming device more comfortable to the patient.

Alternatively, each of the permeable and impermeable sheets comprises a layer of spunbond nonwoven material with a polypropylene extrusion coating on one side. Apertures are formed in one of the sheets, as required for permeability. The extrusion coated sides of the sheets are positioned to face each other, and are sealed, by heat, for example, as required for the construction of the convective warming apparatus. With this construction, the exterior surfaces of the convective warming apparatus are constituted of nonwoven material. The surface of the convective warming apparatus that faces the inside surface of the patient gown is nonwoven, and when the patient slides her or his hands into the hand slits 140, they are in comfortable contact with a soft material.

As suggested in FIGS. 3A and 3B, a patient gown with a poncho-type configuration can be fabricated from a rectangular blank of gown material having a width measured from one side edge to the other of one or more elements of the gown, and a length as required by any particular design. For example, the width of the back panel 110 or the central panel 112 can establish the width of the blank, and the distance between the lower edges 120, 124, the length. Accordingly, patient gowns with a poncho-type configuration can be fabricated in a web-based production line using a patient gown material web of standard width that corresponds to the width of the blank. Further, if the inflatable convective warming apparatus for the patient gown has a rectangular shape with a width less than the width of the blank, elongate, essentially rectangular convective warming devices can also be fabricated in a web-based production line. Thus, patient gowns for a patient warming device in which at least one mode of patient warming is provided by an inflatable convective warming apparatus supported on the inside surface of a poncho-type patient gown can be efficiently and cheaply manufactured in a web-based production line. In the production line, a patient gown material web of standard width that corresponds to the width of the patient gown blank is processed and joined to a convective warming apparatus web.

Figure 6:
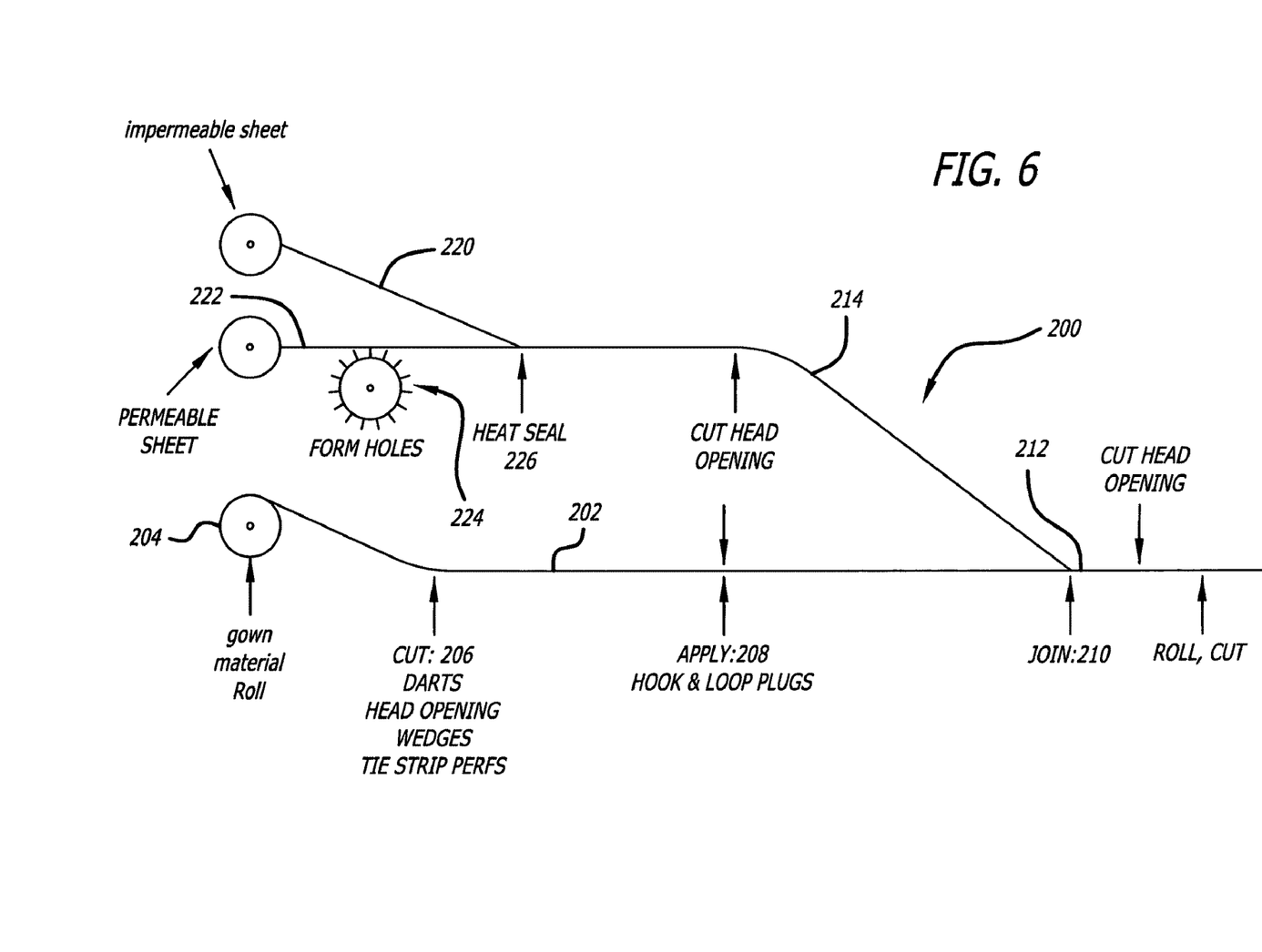
FIG. 6 is a schematic drawing of a web-based production system for manufacturing the preferred warming device embodiment seen in FIGS. 3A and 3B.

For example, patient gowns having the poncho-type configuration of FIGS. 3A and 3B can be fabricated in the web-based production system 200 illustrated in FIG. 6 by feeding a patient gown web 202 from a gown material roll 204 through a shaping station 206 where darts, wedges, hand slits, sleeve slits and/or perforations, and tie strip perforations are die cut. After shaping, the patient gown web 202 is fed through one or more applicator stations 208 where pieces of hook and loop material are attached to both sides of the patient gown web 202, and then through a joining station 210 where a composite web 212 is formed by joining a convective warming apparatus web 214 to the side of the patient gown web 202 that corresponds to the inside surface of the patient gowns. Optionally, the convective warming apparatus web 214 can be fabricated in a separate web-based production line, rolled, and fed to the joining station 210. In either case, the convective warming apparatus web 214 is fabricated by joining a web 220 of gas-impermeable material with a second web 222 of gas-impermeable material that is made gas-permeable by forming holes in the web 222 by means of a spiked roller 224 across which the web 222 is rolled. The webs 220 and 222 are passed through a joining station 226 where the convective warming apparatus web 214 is fabricated by forming peripheral seals, seals for specific features (including head openings), and air channel stake points or seals between the gas-impermeable and gas-permeable material webs 220 and 222. Individual patient gowns with attached convective warming apparatuses can then be cut from the composite web 212. Alternatively, the composite web 212 can be rolled and transported elsewhere for separation of the patient warming devices. Head openings can be formed by die-cutting the patient gown and convective warming apparatus webs 202 and 214 individually, prior to joinder. However, one cutting step can be eliminated, and expense reduced, by die cutting the head openings 116, 166 (and slits 145 and/or transverse perforation lines 146 for sleeve portions) in the composite web 212 by a single step performed after the joining station 210. Expense is further reduced if the single-step die cut includes formation of a pattern of perforations inside the head opening seal 164, without removal of the composite web material within the pattern. In this regard, removal and disposal of the surplus composite web material within the pattern by the user eliminates corresponding fabrication steps.

Figure 7:
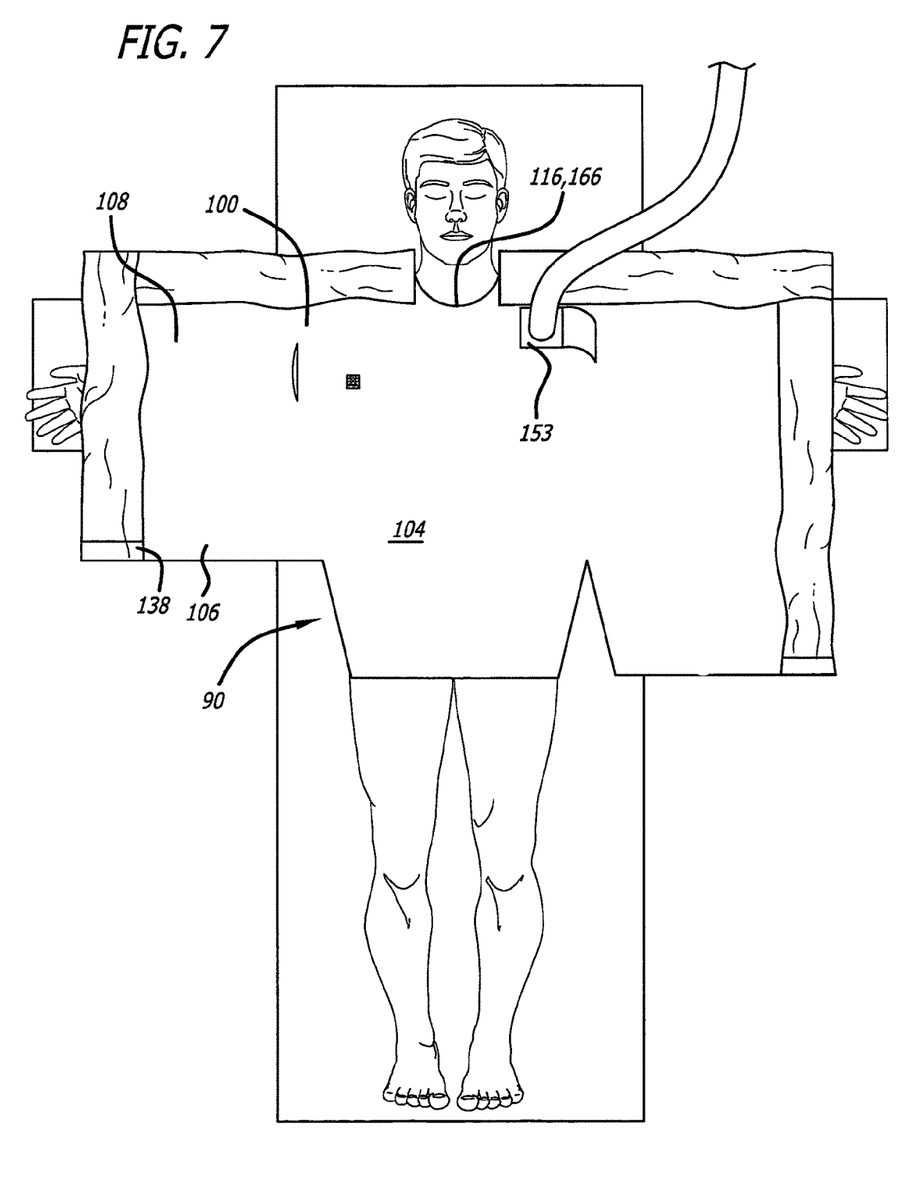
FIG. 7 is an illustration showing a warming device including a poncho-type patient gown with an inflatable convective warming apparatus supported on an inside gown surface which has been opened and deployed in the manner of an upper body thermal blanket for surgery.

FIG. 7 illustrates warming the upper body of a patient by means of a patient warming device in which at least one mode of patient warming is provided by an inflatable convective warming apparatus supported on a poncho-type patient gown. Preferably, but not necessarily, the patient warming device is adapted at least for therapeutic warming. For example, the patient warming device can be constructed as per the patient warming device 90 of FIGS. 3A and 3B, in which therapeutic warming is provided by using the second section 172 in the same manner as an upper body thermal blanket. The view in this figure is toward the outside surface 104 of the patient gown 100, from a position above the patient who is supine on an operating table (not shown), preferably one with cruciate support for the patient's arms. In FIG. 7, the patient warming device 90 is prepared for deployment by releasing the means that hold the sleeve and side edges together. The head opening 116, 166 of the poncho-type configuration enables the patient gown 100, with attached convective warming apparatus 150 to be rotated on the patient's neck and positioned for therapeutic warming, without removal of the patient warming device 90, and retains the patient warming device 90 in position by engagement with the patient's neck. In the therapeutic warming position, the front panel 108 lies longitudinally on the patient's right arm and the back panel 110 lies longitudinally on the patient's left arm. With the patient warming device in this position, the second section 172 extends transversely across the patient's arms, shoulders, and upper chest, with the gas-permeable sheet facing the patient. While the patient is supine, the second section is inflated via the inlet port 153 with a stream of warmed air conditioned for therapeutic warming. When the second section is inflated, warmed air is emitted through the gas-permeable sheet onto the patient. Tie straps 138 can be used to hold the patient warming device 90 closed about the patient's arms and/or secured to the operating table. As shown in FIG. 7, the dimensions of the front, back, and central panels provide ample excess length of gown area to drape from the patient's arms and lower abdomen so as to retain warmed air emitted from the convective warming apparatus under the patient warming device so as to contribute to the desired therapeutic warming of the patient.

Figure 8:
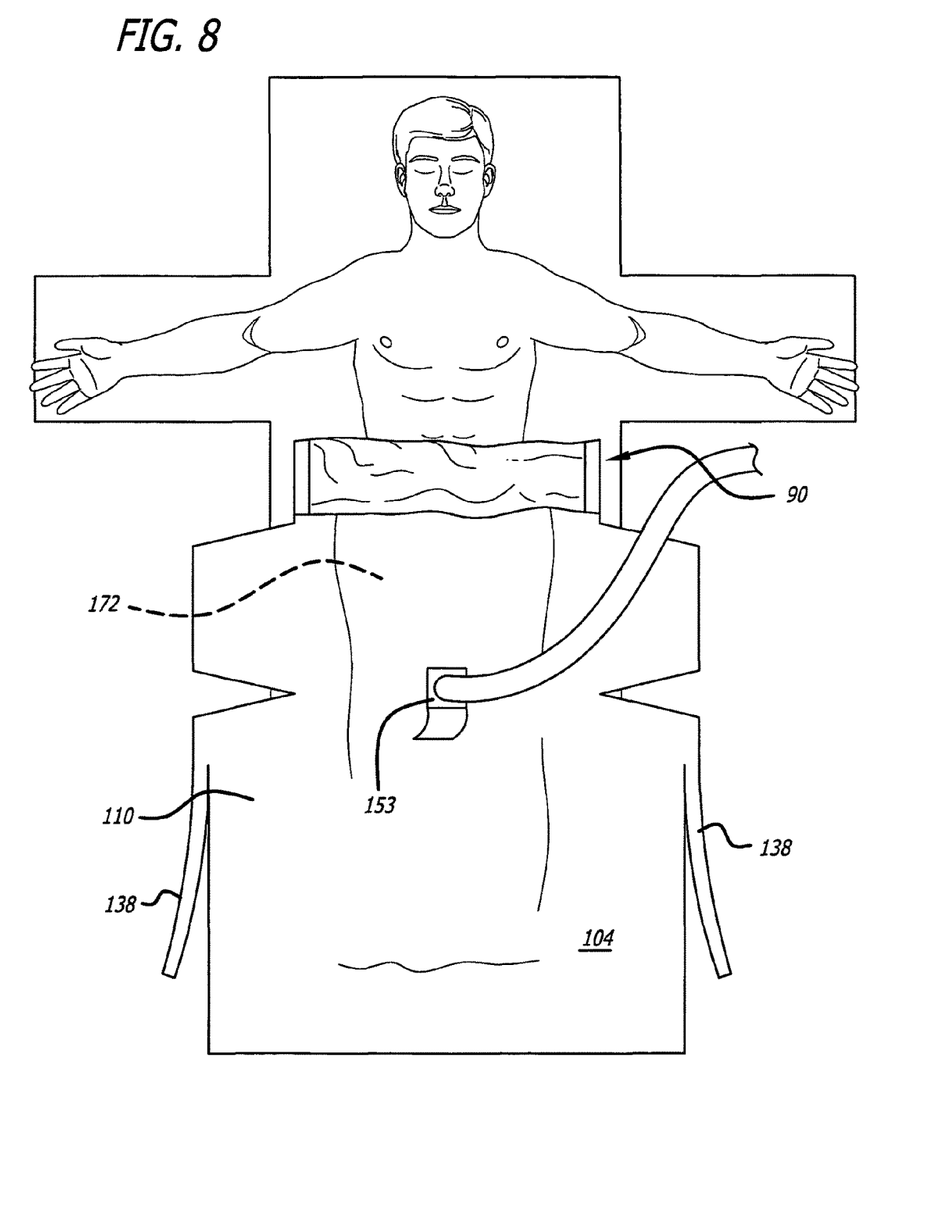
FIG. 8 is an illustration showing a warming device including a poncho-type patient gown with an inflatable convective warming apparatus supported on an inside gown surface which has been opened and deployed in the manner of a full body thermal blanket for surgery.

FIG. 8 illustrates full or lower body warming of a patient by means of a patient warming device in which at least one mode of patient warming is provided by an inflatable convective warming apparatus supported on the inside surface of a poncho-type patient gown. Preferably, but not necessarily, the patient warming device is adapted for therapeutic warming. For example, the patient warming device can be constructed as per the patient warming device 90 of FIGS. 3A and 3B, in which therapeutic warming is provided by using the second section 172 in the same manner as a full or lower body thermal blanket. The view in this figure is toward the outside surface 104 of the patient gown 100, from a position above the patient who is supine on an operating table (not shown). In FIG. 8, the patient warming device 90 is prepared for deployment by releasing the means that hold the sleeve and side edges together and removing the device from the patient by pulling the head opening 116, 166 from the patient's neck. Once removed from the patient, the patient warming device 90 is then positioned for full or lower body therapeutic warming on the patient. In these therapeutic warming positions, the back panel 110 lies longitudinally on the patient, extending from on or near the patient's chest downwardly at least to the patient's abdomen and legs. With the patient warming device in this position, the second section 172 extends longitudinally along the patient's midsection, legs, and feet, with the gas-permeable sheet facing the patient. While the patient is supine, the second section is inflated via the inlet port 153 with a stream of warmed air conditioned for therapeutic warming. When the second section is inflated, warmed air is emitted through the gas-permeable sheet onto the patient. Tie straps 138 can be used to hold the patient warming device 90 closed about the patient's body and/or secured to the operating table. As shown in FIG. 8, the dimensions of the front, back, and central panels provide ample excess length of gown area to drape over the patient's sides and legs so as to retain warmed air emitted from the convective warming apparatus under the patient warming device so as to contribute to the desired therapeutic warming.

Preferred PATIENT WARMING DEVICE CONSTRUCTIONS WITH A PONCHO-TYPE PATIENT GOWN which have been shown and described in detail fully achieve the objects of the invention. Nevertheless, the described embodiments are merely examples representative of the subject matter which is broadly comprehended by the invention. And so the scope of the invention fully encompasses other embodiments which may become obvious to those skilled in the art. Therefore, the scope of the invention is to be limited by no more than the following claims, in which reference to an element in the singular is not intended to mean "one and only one", but rather is intended to mean "at least one". It is not necessary for a patient warming device or method to address each and every problem sought to be solved by the present invention, for it to be encompassed by the claims. Furthermore, no element, component, or method step in the disclosure is intended to be dedicated to the public regardless of whether the element, component, or method step is explicitly recited in the claims. Absent express definitions set forth in the detailed description, claim terms are to be given ordinary and accustomed meanings that are not irreconcilable with the specification and file history.

The invention claimed is:

1. A patient gown in a patient warming device in which at least one mode of patient warming is provided by an inflatable convective warming apparatus supported on the inside surface of a poncho-type patient gown including a major body portion with inside and outside surfaces, front and back panels, a central panel joining the front and back panels, sleeve portions on opposing sides of the central panel, and a head opening in the central panel, between the sleeve portions, the inflatable convective warming apparatus extending along the front and central panels at least to the head opening, and at least one inlet port opening through an impermeable portion of the inflatable convective warming apparatus.

2. The patient gown in a patient warming device according to claim 1, in which the inflatable convective warming apparatus includes an impermeable sheet of material and a permeable sheet of material sealed together by at least a peripheral seal, the impermeable sheet of material is attached to the inside surface of the patient gown, and the at least one inlet port is in the impermeable sheet of material.

3. The patient gown in a patient warming device according to claim 2, in which the inflatable convective warming apparatus includes separately inflatable sections, and the at least one inlet port includes at least one inlet port into a first section and at least one inlet port into a second section.

4. The patient gown in a patient warming device according to claim 3, in which the first section includes a first volume and the second section includes a second volume greater than the first volume.

5. The patient gown in a patient warming device according to claim 3, in which the first section includes a first portion of the permeable sheet of material having a first permeability and the second section includes a second portion of the permeable sheet of material having a second permeability greater than the first permeability.

6. The patient gown in a patient warming device according to claim 1, in which the inflatable convective warming apparatus includes an impermeable sheet of material and a permeable sheet of material sealed to the sheet of impermeable material along a common periphery, the sheet of impermeable material is attached to the inside surface, and the at least one inlet port includes a collar of stiff material attached to the sheet of impermeable material, around an opening in the sheet of impermeable material.

7. The patient gown in a patient warming device according to claim 6, in which the inflatable convective warming apparatus includes first and second separately inflatable sections, the first section has a first permeability and the second section has a second permeability, greater than the first permeability, the first section includes at least one inlet port, and the second section includes at least one inlet port, and further includes a first opening through the front panel in alignment with a portion of the inflatable convective warming apparatus where the at least one inlet port of the first section is positioned, and a second opening through the back panel in alignment with a portion of the inflatable convective warming apparatus where the at least one inlet port of the second section is positioned.

8. The patient gown in a patient warming device according to claim 6, further including hand slits in the front panel.

9. The patient gown in a patient warming device according to claim 6, further including tie straps on side edges the front and back panels.

10. The patient gown in a patient warming device according to claim 6, further including at least one of elongate longitudinal slits and transverse perforation lines in the central panel, between opposing edges of each sleeve portion.

11. The patient gown in a patient warming device according to claim 6, further including at least one opening through the front panel in alignment with a portion of the inflatable convective warming apparatus where the at least one inlet port is positioned.

12. The patient gown in a patient warming device according to claim 1, in which the inflatable convective warming apparatus includes a permeable sheet of material attached at least along its periphery to the inside surface of the patient gown, and the at least one inlet port is attached to the outside surface of the patient gown in communication with an opening in the front panel.

13. The patient gown in a patient warming device according to claim 12, in which the inflatable convective warming apparatus includes separately inflatable sections, and the at least one inlet port includes at least one inlet port into a first section and at least one inlet port into a second section.

14. The patient gown in a patient warming device according to claim 13, in which the first section includes a first volume and the second section includes a second volume greater than the first volume.

15. The patient gown in a patient warming device according to claim 13, in which the first section includes a first portion of the permeable sheet of material having a first permeability and the second section includes a second portion of the permeable sheet of material having a second permeability greater than the first permeability.

16. A patient gown in a patient warming device in which two modes of patient warming are provided by an inflatable convective warming apparatus supported on the inside surface of a poncho-type patient gown including a major body portion with inside and outside surfaces, front and back panels, a central panel joining the front and back panels, sleeve portions on opposing sides of the central panel, and a head opening in the central panel, between the sleeve portions, the inflatable convective warming apparatus extending along the front, central, and back panels and including a head opening in alignment with the head opening in the patient gown, and at least one inlet port opening through an impermeable portion of the inflatable convective warming apparatus.

17. The patient gown in a patient warming device according to claim 16, in which the inflatable convective warming apparatus includes an impermeable sheet of material and a permeable sheet of material sealed together by at least a peripheral seal, in which the impermeable sheet of material is attached to the inside surface of the patient gown and the at least one inlet port opens through the impermeable sheet of material.

18. The patient gown in a patient warming device according to claim 17, in which the inflatable convective warming, apparatus includes separately inflatable comfort and therapeutic warming sections, the comfort warming section is positioned along a portion of the front panel and the therapeutic warming section extends along the front, central, and back panels and includes a head opening aligned with the central panel head opening, and the at least one inlet port includes at least one inlet port into the comfort warming section and at least one inlet port into the therapeutic warming section.

19. The patient gown in a patient warming device according to claim 18, in which the comfort warming section includes a first volume of inflatable space and the therapeutic warming section includes a second volume of inflatable space greater than the first volume.

20. The patient gown in a patient warming device according to claim 18, in which the comfort warming section includes a first portion of the permeable sheet of material having a first permeability and the therapeutic warming section includes a second portion of the permeable sheet of material having a second permeability greater than the first permeability.

21. The patient gown in a patient warming device according to claim 16, further including hand slits in the front panel.

22. The patient gown in a patient warming device according to claim 16, further including tie straps on side edges of the front and back panels.

23. The patient gown in a patient warming device according to claim 16, further including at least one of an elongate longitudinal slit and a transverse perforation line in each sleeve portion, between opposing edges of each sleeve portion.

24. The patient gown in a patient warming device according to claim 16, further including at least one opening through the front panel in alignment with a portion of the inflatable convective warming apparatus where the at least one inlet port is positioned.

25. A method of warming a patient with a warming device which includes a poncho-type patient gown with a central panel, a head opening in the central panel, and an inflatable convective warming apparatus supported on an inside surface of the patient gown and extending along the front panel at least to the head opening, the method comprising:
  clothing a patient in the poncho-type patient gown such that the patient's head is received in the head opening;
  releasably attaching opposing sides of the patient gown;
  inflating the convective warming apparatus with a stream of warmed air;
  wherein warmed air is expelled from the convective warming apparatus onto the patient;
  separating the opposing sides;
  rotating the poncho-type patient gown about the patient's head to position the patient gown across the patient's arms when the patient is supine; and,
  while the patient is supine, inflating the convective warming apparatus with a stream of warmed air;
  wherein warmed air is emitted from the convective warming apparatus onto the patient.

26. A method of manufacturing warming devices in which each warming device includes a patient gown with an inflatable convective warming apparatus supported on a surface of the patient gown, comprising the acts of:
  forming patient gowns with poncho-type configurations in a patient gown web;
  forming inflatable convective warming apparatuses in a convective warming apparatus web;
  joining the convective warming apparatus web to a predetermined surface of the patient gown web to form a composite web.

27. The method of manufacturing according to claim 26, in which:
  forming patient gowns with poncho-type configurations includes forming head openings in the patient gown web; and,
  forming inflatable convective warming apparatuses includes forming head openings in the convective warming apparatus web.

28. The method of manufacturing according to claim 26, further including forming head openings in the composite web.

* * * * *

UNITED STATES PATENT AND TRADEMARK OFFICE
CERTIFICATE OF CORRECTION

PATENT NO. : 8,192,475 B2  
APPLICATION NO. : 12/653825  
DATED : June 5, 2012  
INVENTOR(S) : Thomas P Anderson Page 1 of 1

It is certified that error appears in the above-identified patent and that said Letters Patent is hereby corrected as shown below:

Title Page 2, Column 2,  
Item [56] under "Other Publications", line 13, after "Hooker" insert -- 128/897 --.

Title Page 2, Column 2,  
Item [56] under "Other Publications", line 15, after "Gross et al." insert -- 2/458 --.

Page 2, Column 2,  
Item [56] under "Other Publications", line 62, after "Malmberg et al." insert -- 607/104 --.

In the Specification

Column 1,  
Line 43, delete "No" and insert -- No. --, therefor.

Column 3,  
Line 26, delete "Anestheseology" and insert -- Anesthesiology --, therefor.

Column 6,  
Line 29, delete "body" and insert -- body. --, therefor.

In the Claims

Column 14,  
Line 57, in claim 9, after "edges" insert -- of --.

Signed and Sealed this  
Seventeenth Day of December, 2013

Margaret A. Focarino  
*Commissioner for Patents of the United States Patent and Trademark Office*